United States Patent
Chong et al.

(12) 
(10) Patent No.: US 6,307,094 B1
(45) Date of Patent: Oct. 23, 2001

(54) PROCESS FOR SUBSTITUTED 3-HYDROXYBUTYRATE ESTERS

(76) Inventors: Joshua Anthony Chong, 112 Field Ter., Lansdale, PA (US) 19446; Fereydon Abdesaken, 269 Westwind Way, Dresher, PA (US) 19025; Lori Ann Spangler, 115 Elm Ave., Churchville, PA (US) 18966; Renee Caroline Roemmele, 1030 Fulton Rd., Maple Glen, PA (US) 19002; Randall Wayne Stephens, 114 Stoneycrest Dr., Perkasie, PA (US) 18944; Peter David Nightingale, Vale Cottage Millbrow, Marple Bridge Stockport SK6 5LW (GB); David John Hartley, 4 Belmont Street, Monton Eccles, Manchester, M30 9NZ (GB)

( * ) Notice: Subject to any disclaimer, the term of this patent is extended or adjusted under 35 U.S.C. 154(b) by 0 days.

(21) Appl. No.: 09/564,656

(22) Filed: May 2, 2000

Related U.S. Application Data

(60) Provisional application No. 60/133,434, filed on May 11, 1999.

(51) Int. Cl.$^7$ ...................................................... C07C 69/63
(52) U.S. Cl. ................................. 560/184; 562/586; 562/2
(58) Field of Search ...................................... 560/192, 184, 560/226; 556/135, 2, 586

(56) References Cited

U.S. PATENT DOCUMENTS 4,933,482   6/1990   Sayo et al. .

FOREIGN PATENT DOCUMENTS 8-79046   4/1996   (JP) .

OTHER PUBLICATIONS

G. Kathawala et al., Helvetica Chimica Acta–vol. 69, (1986).

*Primary Examiner*—Gary Geist
*Assistant Examiner*—Zachary Tucker
(74) *Attorney, Agent, or Firm*—Clark R. Carpenter

(57) ABSTRACT

The present invention provides a solventless process for the catalytic hydrogenation of esters of 4,4,4-trihaloacetoacetic acid using a platinum catalyst in the presence of an acid or base co-catalyst to provide the analagous 3-hydroxybutyrate ester. Such 3-hydroxybutyrate esters are useful as solvents, cleaners or fine chemical intermediates.

16 Claims, No Drawings

PROCESS FOR SUBSTITUTED 3-HYDROXYBUTYRATE ESTERS

This Application claims benefit of provisional No. 60/133,434 filed May 11, 1999.

The present invention relates to a process for the reduction of esters of 4,4,4-trihaloacetoacetic acid and derivatives. The process involves catalytic hydrogenation in the absence of a solvent using a platinum catalyst and is co-catalyzed by the addition of an acid or a base. The resulting product 3-hydroxybutyrate esters are useful as solvents or cleaners, or as fine chemical intermediates to pharmaceuticals, agricultural chemicals, liquid crystals, and dyes.

There are a number of ways of reducing β-ketoesters which have been disclosed. In addition to hydrogenation, reduction with zinc/acetic acid or with borohydride reagents are known. For the hydrogenation reactions reported in the literature, most use ruthenium, nickel, or baker's yeast as catalyst. All use a solvent. F. G. Kathawala et al. in *Helvetica Chimica Acta*, 69, 803–805 (1986) disclose an example in which 5% platinum on carbon is used as a catalyst for the reduction of various β-ketoesters using methanol as a solvent. T. Fujima et al. in JP 09268146 A2, Oct. 14, 1997 disclose the hydrogenation of ethyl trifluoroacetoacetate using a nickel catalyst in tetrahydrofuran solvent to provide ethyl 4,4,4-trifluoro-3-hydroxybutyrate in 78% yield. N. Sayo et al. in U.S. 4,933,482, Jun. 12, 1990 disclose the hydrogenation of ethyl trifluoroacetoacetate using a ruthenium catalyst in a polar solvent such as an alcohol or tetrahydrofuran to provide ethyl 4,4,4-trifluoro-3-hydroxybutyrate in 95% yield. None of these references disclose or suggest the process of the present invention in which we have discovered that no solvent is necessary for the catalytic hydrogenation.

The advantages of not using a solvent in the hydrogenation process are:

(1) lower cost preparation of the product because no solvent has to be added,
(2) lower waste disposal costs,
(3) the need for solvent recycle is eliminated,
(4) higher yields of desired product result,
(5) higher process reactor productivity because of reduced volume,
(6) product purification is facilitated since the practitioner needs to only filter away the catalyst to obtain pure product without the need to distill solvent or product,
(7) lower catalysts loads are required for productive hydrogenation, and
(8) the process can be made a continuous process by flowing starting material over a bed of immobilized catalyst.

Accordingly, this invention provides a process for the preparation of a compound of formula (I)

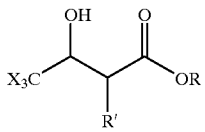

(I)

from a compound of formula (II)

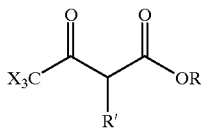

(II)

without a reaction solvent being present which comprises the steps of (i) reacting the compound of formula (II) with hydrogen in the presence of a catalytic amount of platinum and a catalytic amount of an acid or base to form the compound of formula (I), and
(ii) separating the compound of formula (I) from the platinum catalyst, wherein X is fluoro or chloro,
R is alkyl, haloalkyl, polyhaloalkyl, alkyl substituted with $NR^2R^3$, hydroxy or $OR^4$, phenyl or phenyl substituted with one or more groups independently selected from halo, alkyl, hydroxy, alkoxy, haloalkoxy, polyhaloalkoxy, haloalkyl or polyhaloalkyl,
R' is a hydrogen atom, alkyl, haloalkyl, polyhaloalkyl, alkyl substituted with $NR^2R^3$, hydroxy or $OR^4$, phenyl or phenyl substituted with one or more groups independently selected from halo, alkyl, hydroxy, alkoxy, haloalkoxy, polyhaloalkoxy, haloalkyl or polyhaloalkyl, $R^2$ and $R^3$ are each independently a hydrogen atom, alkyl, or together with the nitrogen atom to which they are attached form a 5- or 6-membered heterocyclic ring, and
$R^4$ is alkyl, haloalkyl or polyhaloalkyl.

As used herein, the term "alkyl" refers to straight and branched aliphatic hydrocarbon chains, for example, methyl, ethyl, n-propyl, isopropyl, n-butyl, sec-butyl, tert-butyl, isoamyl and n-hexyl.

The term "alkoxy" refers to straight and branched aliphatic hydrocarbon chains attached to an oxygen atom, for example, methoxy, ethoxy, n-propoxy, isopropoxy and n-butoxy.

The term "haloalkyl" refers to a straight or branched aliphatic hydrocarbon chain substituted with a fluoro, chloro or bromo, for example chloromethyl, 2-fluoroethyl and 4-bromobutyl.

The term "polyhaloalkyl" refers to a straight or branched aliphatic hydrocarbon chain multiply substituted with a fluoro or chloro, for example difluoromethyl, trifluoromethyl, 1,1,2,2,2-pentafluoroethyl and trichloromethyl.

The term "haloalkoxy" refers to a straight or branched aliphatic hydrocarbon chain, attached to an oxygen atom, substituted with a fluoro, chloro or bromo, for example fluoromethoxy, 2-chloroethoxy and 4-bromobutoxy.

The term "polyhaloalkoxy" refers to a straight or branched aliphatic hydrocarbon chain, attached to an oxygen atom, multiply substituted with a fluoro or chloro, for example difluoromethoxy, trifluoromethoxy, 1,1,2,2,2-pentafluoroethoxy and trichloromethoxy.

In a preferred process of this invention,
X is fluoro or chloro,
R is $(C_1-C_4)$alkyl, halo$(C_1-C_4)$alkyl, polyhalo$(C_1-C_4)$alkyl, $(C_1-C_4)$alkyl substituted with $NR^2R^3$, hydroxy or $OR^4$, phenyl or phenyl substituted with one or more groups independently selected from halo, $(C_1-C_2)$ alkyl, hydroxy, $(C_1-C_2)$ alkoxy, halo $(C_1-C_2)$ alkoxy, polyhalo $(C_1-C_2)$ alkoxy, halo$(C_1-C_2)$alkyl or polyhalo$(C_1-C_2)$alkyl, R' is a hydrogen atom, $(C_1-C_4)$alkyl, halo$(C_1-C_4)$alkyl, polyhalo$(C_1-C_4)$alkyl, $(C_1-C_4)$alkyl substituted with $NR^2R^3$, hydroxy or $OR^4$, phenyl or phenyl substituted with one or more groups independently selected from halo, $(C_1-C_2)$alkyl, hydroxy, $(C_1-C_2)$alkoxy, h halo $(C_1-C_2)$alkyl or polyhalo$(C_1-C_2)$alkyl, $R^2$ and $R^3$ are each independently a hydrogen atom, $(C_1-C_2)$alkyl, or together with the nitrogen atom to which they are attached form a 5- or 6-membered heterocyclic ring, and $R^4$ is $(C_1-C_2)$alkyl, halo$(C_1-C_2)$alkyl or polyhalo$(C_1-C_2)$ alkyl.

In a more preferred process of this invention,

X is fluoro,

R is $(C_1-C_3)$alkyl, polyhalo$(C_1-C_2)$alkyl or $(C_1-C_2)$alkyl substituted with $OR^4$, R' is a hydrogen atom, $(C_1-C_2)$alkyl, polyhalo$(C_1-C_2)$ alkyl, $(C_1-C_2)$alkyl substituted with $NR^2R^3$, hydroxy or $OR^4$, $R^2$ and $R^3$ are each independently a hydrogen atom, $(C_1-C_2)$alkyl, or together with the nitrogen atom to which they are attached form a 5- or 6-membered heterocyclic ring, and $R^4$ is $(C_1-C_2)$alkyl or polyhalo$(C_1-C_2)$alkyl.

In an even more preferred process of this invention, R is methyl or ethyl and R' is a hydrogen atom, $(C_1-C_2)$alkyl or polyhalo$(C1-C_2)$alkyl.

In a most preferred process of this invention, R is ethyl and R' is a hydrogen atom.

The catalytic amount of platinum can be any form of platinum with a high surface area. Such catalysts may take the form of platinum on a carbon support, preferably 5% by weight of platinum on carbon (5% Pt/C), platinum on an alumina support, platinum on a silica support, platinum on a ceramic support, platinum(IV) oxide ($PtO_2$) or a fluidized bed. The catalyst load can range from 0.001 to 10%, preferably from 0.001 to 0.1%, more preferably from 0.001 to 0.05% and even more preferably from 0.01 to 0.05%. The catalyst load is measured as the weight of platinum relative to the weight of 4,4,4-trihaloacetoacetate starting material. Other metals have been explored as catalysts, including Raney nickel, palladium on carbon, and ruthenium on carbon. Only very low yields of a 4,4,4-trihalo-3-hydroxybutyrate ester product were obtained (0–25%)

The hydrogen pressure can range from 1 to 100 bars, preferably from 2 to 5 bars. The reduction reaction temperature can range from ambient to 150° C., preferably from ambient to 80° C., more preferably from 30 to 60° C. Reaction times are dependent on the reactor design, reaction temperature, hydrogen pressure, etc. but are usually from 1 to 24 hours, preferably from 2 to 10 hours. Good agitation of the reaction mixture leads to shorter reaction times.

A base or acid is added as a co-catalyst. Loading of the co-catalyst can be from 0.1 to 10% by weight relative to the weight of trihaloacetoacetate starting material. Preferred is from 0.1 to 3% by weight. The co-catalyst can be a soluble or insoluble acid or base. Bases are more preferable than acids as co-catalyst. Examples of acid co-catalysts are organic or inorganic acids such as HCl, $H_2SO_4$, p-toluenesulfonic acid, methanesulfonic acid, acetic acid, trichloroacetic acid, a cation-exchange resin, etc. Examples of bases are organic or inorganic bases such as triethylamine (and other mono-, di-, and trialkylamines), pyridine and substituted pyridines, hydroxides, carbonates, bicarbonates, an anion-exchange resin, etc. Preferred bases are triethylamine and mono-, di- and trialkylamines. If very high purity 4,4,4-trihalo-3-hydroxybutyrate ester product is desired, it may be best to use insoluble bases such as poly (vinylpyridine) or an anion-2,7) exchange resin which can be removed from the product by filtration.

The process can be run as a batch reaction, in which 4,4,4-trihaloacetoacetate starting material, platinum catalyst and co-catalyst are charged, the reactor is charged with hydrogen gas and agitated to produce product. The product is then isolated by filtration, centrifugation or other suitable means to remove catalyst. The process could also be performed in a semi-continuous fashion, in which 4,4,4-trihaloacetoacetate starting material containing the co-catalyst is passed over a bed of immobilized catalyst, and pure product collected at the end. The catalyst bed should be made in such a way as to provide mechanical stability and a high surface area of platinum. The support material could be carbon, alumina, ceramic or other materials. The reaction can be heated in either mode of operation.

The following examples and experimental procedures are provided for additional guidance to the practitioner.

EXAMPLE 1

Preparation of Ethyl 4,4,4-Trifluoro-3-Hydroxybutyrate

Ethyl 4,4,4-trifluoroacetoacetate (350 g), under a blanket of nitrogen gas, was heated to 40° C. and treated with platinum (0.7 g of 5% Pt/C, 0.01% load) and triethylamine (1.5 g, 0.4% load). Hydrogen was charged to a pressure of 5 bars and the mixture agitated at 40° C. for 6h. After filtration to remove the catalyst, 341 g (96% yield) of ethyl 4,4,4-trifluoro-3-hydroxybutyrate was obtained.

EXAMPLE 2

Preparation of Ethyl 4,4,4-Trifluoro-3-Hydroxybutyrate

Ethyl 4,4,4-trifluoroacetoacetate (50 g), under a blanket of nitrogen gas, was heated to 40° C. and treated with platinum (0.1 g of 5% Pt/C, 0.01% load) and triethylamine (1.5 g, 2.9% load). Hydrogen was charged to a pressure of 5 bars, and the mixture agitated at 40° C. for 6h. After filtration to remove the catalyst, 48.5 g (96% yield) of ethyl 4,4,4-trifluoro-3-hydroxybutyrate was obtained.

EXAMPLE 3

Preparation of Ethyl 2-Methyl-4,4,4-Trifluoro-3-Hydroxybutyrate

Ethyl 2-methyl-4,4,4-trifluoroacetoacetate (50 g), under a blanket of nitrogen gas, is heated to 40° C. and treated with platinum (0.1 g of 5% Pt/C, 0.01% load) and triethylamine (0.2 g, 0.4 % load). Hydrogen is charged to a pressure of 5 bars, and the mixture agitated at 40° C. for 6h. After filtration to remove the catalyst, 48.5 g (96% yield) of ethyl 2-methyl-4,4,4-trifluoro-3-hydroxybutyrate is obtained.

EXAMPLE 4

Preparation of Ethyl 4,4,4-Trifluoro-3-Hydroxybutyrate

Ethyl 4,4,4-trifluoroacetoacetate (50 g), under a blanket of nitrogen gas, is heated to 40° C. and treated with platinum (0.1 g of 5% Pt/C, 0.01% load) and methanesulfonic acid (1.5 g, 2.9% load). Hydrogen is charged to a pressure of 5 bars, and the mixture agitated at 40° C. for 6h. After filtration to remove the catalyst, 25.3 g (50% yield) of ethyl 4,4,4-trifluoro-3-hydroxybutyrate is obtained.

EXAMPLE 5

Preparation of Ethyl 4,4,4-Trifluoro-3-Hydroxybutyrate

Ethyl 4,4,4-trifluoroacetoacetate (50 g), under a blanket of nitrogen gas, is heated to 40° C. and treated with platinum (0.5 g of 1% Pt/C, 0.05% load) and triethylamine (0.2 g, 0.4% load). Hydrogen is charged to a pressure of 5 bars, and the mixture agitated at 40° C. for 6h. After filtration to remove the catalyst, 48.5 g (96% yield) of ethyl 4,4,4-trifluoro-3-hydroxybutyrate is obtained.

EXAMPLE 6

Preparation of Ethyl 4,4,4-Trifluoro-3-Hydroxybutyrate

Ethyl 4,4,4-trifluoroacetoacetate (50 g), under a blanket of nitrogen gas, is heated to 40° C. and treated with platinum (0.1 g of 5% Pt/alumina, 0.01% load) and triethylamine (0.2 g, 0.4% load). Hydrogen is charged to a pressure of 5 bars, and the mixture agitated at 40° C. for 6h. After filtration to remove the catalyst, 48.5 g (96% yield) of ethyl 4,4,4-trifluoro-3-hydroxybutyrate is obtained.

EXAMPLE 7

Preparation of Isopropyl 4,4,4-Trifluoro-3-Hydroxybutyrate

Isopropyl 4,4,4-trifluoroacetoacetate (50 g), under a blanket of nitrogen gas, is heated to 40° C. and treated with platinum (0.1 g of 5% Pt/C, 0.01% load) and triethylamine (0.2 g, 0.4 % load). Hydrogen is charged to a pressure of 5 bars, and the mixture agitated at 40° C. for 6h. After filtration to remove the catalyst, 48.5 g (96% yield) of isopropyl 4,4,4-trifluoro-3-hydroxybutyrate is obtained.

We claim:

1. A process for the preparation of a compound of formula (I)

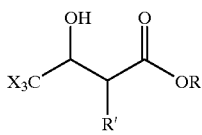

(I)

from a compound of formula (II)

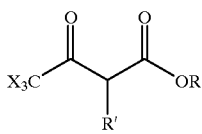

(II)

without a reaction solvent being present which comprises the steps of
(i) reacting the compound of formula (II) with hydrogen in the presence of a catalytic amount of platinum and a catalytic amount of an acid or a base to form the compound of formula (I), and
(ii) separating the compound of formula (I) from the platinum catalyst, wherein X is fluoro or chloro, R is alkyl, haloalkyl, polyhaloalkyl, alkyl substituted with $NR^2R^3$, hydroxy or $OR^4$, phenyl or phenyl substituted with one or more groups independently selected from halo, alkyl, hydroxy, alkoxy, haloalkoxy, polyhaloalkoxy, haloalkyl or polyhaloalkyl, R' is a hydrogen atom, alkyl, haloalkyl, polyhaloalkyl, alkyl substituted with $NR^2R^3$, hydroxy or $OR^4$, phenyl or phenyl substituted with one or more groups independently selected from halo, alkyl, hydroxy, alkoxy, haloalkoxy, polyhaloalkoxy, haloalkyl or polyhaloalkyl, $R^2$ and $R^3$ are each independently a hydrogen atom, alkyl, or together with the nitrogen atom to which they are attached form a 5- or 6-membered heterocyclic ring, and $R^4$ is alkyl, haloalkyl or polyhaloalkyl.

2. The process of claim 1 wherein

X is fluoro or chloro,

R is $(C_1-C_4)$alkyl, halo$(C_1-C_4)$alkyl, polyhalo$(C_1-C_4)$alkyl, $(C_1-C_4)$alkyl substituted with $NR^2R^3$, hydroxy or $OR^4$, phenyl or phenyl substituted with one or more groups independently selected from halo, $(C_1-C_2)$alkyl, hydroxy, $(C_1-C_2)$alkoxy, halo$(C_1-C_2)$alkoxy, polyhalo$(C_1-C_2)$alkoxy, halo$(C_1-C_2)$alkyl or polyhalo$(C_1-C_2)$alkyl, R' is a hydrogen atom, $(C_1-C_4)$alkyl, halo$(C_1-C_4)$alkyl, polyhalo$(C_1-C_4)$alkyl, $C_1-C_4)$alkyl substituted with $NR^2R^3$, hydroxy or $OR^4$, phenyl or phenyl substituted with one or more groups independently selected from halo, $(C_1-C_2)$alkyl, hydroxy, $(C_1-C_2)$ alkoxy, halo $(C_1-C_2)$alkoxy, polyhalo$(C_1-C_2)$alkoxy, halo$(C_1-C_2)$alkyl or polyhalo$(C_1-C_2)$alkyl, $R^2$ and $R^3$ are each independently a hydrogen atom, $(C_1-C_2)$alkyl, or together with the nitrogen atom to which they are attached form a 5- or 6-membered heterocyclic ring, and $R^4$ is $(C_1-C_2)$alkyl, halo$(C_1-C_2)$alkyl or polyhalo$(C_1-C_2)$alkyl.

3. The process of claim 2 wherein

X is fluoro,

R is $(C_1-C_3)$alkyl, polyhalo$(C_1-C_2)$alkyl or $(C_1-C_2)$alkyl substituted with $OR^4$, R' is a hydrogen atom, $(C_1-C_2)$alkyl, polyhalo$(C1-C_2)$alkyl, $(C_1-C_2)$alkyl substituted with $NR^2R^3$, hydroxy or $OR^4$, $R^2$ and $R^3$ are each independently a hydrogen atom, $(C_1-C_2)$alkyl, or together with the nitrogen atom to which they are attached form a 5- or 6-membered heterocyclic ring, and $R^4$ is $(C_1-C_2)$alkyl or polyhalo$(C_1-C_2)$alkyl.

4. The process of claim 3 wherein R is methyl or ethyl and R' is a hydrogen atom, $(C_1-C_2)$alkyl or polyhalo$(C_1-C_2)$alkyl.

5. The process of claim 4 wherein R is ethyl and R' is a hydrogen atom.

6. The process as in any one of the preceding claims in which the catalytic amount of platinum in step (i) is selected from the group consisting of platinum on a carbon support, platinum on an alumina support, platinum on a silica support, platinum on a ceramic support and platinum(IV) oxide.

7. The process of claim 6 wherein the catalytic amount of platinum is 5% by weight platinum on a carbon support.

8. The process of claim 6 wherein the catalytic amount of an acid or a base is selected from the group consisting of HCl, $H_2SO_4$, p-toluenesulfonic acid, methanesulfonic acid, acetic acid, trichloroacetic acid, a cation-exchange resin, a monoalkylamine, a dialkylamine, a trialkylamine, pyridine, a substituted pyridine, a hydroxide, a carbonate, a bicarbonate, an anion-exchange resin and poly(vinylpyridine).

9. The process of claim 8 wherein the base is a dialkylamine or a trialkylamine.

10. The process of claim 9 wherein the amine is triethylamine.

11. The process of claim 8 wherein the acid or base is present in an amount from 0.1 to 10% by weight relative to the weight of the compound of formula (II).

12. The process of claim 6 wherein the catalytic amount of platinum is present in an amount from 0.001 to 10% by weight relative to the weight of the compound of formula (II).

13. The process of claim 12 wherein the catalytic amount of platinum is present in an amount from 0.001 to 0.1% by weight.

14. The process of claim 6 wherein the hydrogen pressure is from 1 to 100 bars.

15. The process of claim 6 wherein the reaction temperature is from ambient to 150° C.

16. The process of claim 15 wherein the reaction temperature is from ambient to 80° C.

* * * * *